United States Patent
Reynolds (10) Patent No.: US 8,574,225 B2
(45) Date of Patent: *Nov. 5, 2013

(54) EFFICIENT CONTROLLED CRYOGENIC FLUID DELIVERY INTO A BALLOON CATHETER AND OTHER TREATMENT DEVICES

(75) Inventor: Bryron Reynolds, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 843 days.

This patent is subject to a terminal disclaimer.

(21) Appl. No.: 12/582,454

(22) Filed: Oct. 20, 2009

(65) Prior Publication Data

US 2010/0042086 A1 Feb. 18, 2010

Related U.S. Application Data

(63) Continuation of application No. 11/013,937, filed on Dec. 15, 2004, now Pat. No. 7,604,631.

(51) Int. Cl.
*A61B 18/02* (2006.01)

(52) U.S. Cl.
USPC .......................... 606/20; 251/129.15

(58) Field of Classification Search
USPC ...................... 128/898; 606/20–26
See application file for complete search history.

(56) References Cited

U.S. PATENT DOCUMENTS

| | | | |
|---|---|---|---|
| 3,125,096 A | | 3/1964 | Antiles et al. |
| 3,823,575 A | * | 7/1974 | Parel .............................. 62/51.2 |
| 3,901,241 A | | 8/1975 | Allen, Jr. |
| RE28,657 E | * | 12/1975 | Barger et al. .................... 606/23 |
| 4,336,691 A | | 6/1982 | Burstein et al. |
| 4,754,752 A | | 7/1988 | Ginsburg et al. |
| 4,946,460 A | * | 8/1990 | Merry et al. .................... 606/24 |
| 5,019,075 A | | 5/1991 | Spears et al. |
| 5,041,089 A | | 8/1991 | Mueller et al. |
| 5,078,713 A | | 1/1992 | Varney |
| 5,092,841 A | | 3/1992 | Spears |
| 5,106,360 A | | 4/1992 | Ishiwara et al. |
| 5,147,355 A | | 9/1992 | Friedman et al. |
| 5,151,100 A | | 9/1992 | Abele et al. |
| 5,190,539 A | | 3/1993 | Fletcher et al. |

(Continued)

FOREIGN PATENT DOCUMENTS

WO 91/05528 A1 5/1991
WO 98/38934 A1 9/1998

(Continued)

OTHER PUBLICATIONS

Gage, M.D., Andrew A., et al., "Freezing injury to large blood vessels in dogs," Surgery, vol. 61, No. 5, May 1967, pp. 748-754.

*Primary Examiner* — Bill Thomson
*Assistant Examiner* — Lynsey Crandall
(74) *Attorney, Agent, or Firm* — Vidas, Arrett & Steinkraus, P.A.

(57) ABSTRACT

Devices, systems, and methods efficiently dilate and/or cool blood vessels and other body tissues. Controlled cooling with balloon catheters and other probes may be effected by a change in phase of a cryogenic fluid, often after measuring a minimum pulse width for actuating an individual solenoid valve along the cooling fluid path, with the measured pulse width allowing gradual inflation of a balloon without excessive venting of cooling fluid.

20 Claims, 8 Drawing Sheets

(56) References Cited

U.S. PATENT DOCUMENTS

| | | |
|---|---|---|
| 5,191,883 A | 3/1993 | Lennox et al. |
| 5,196,024 A | 3/1993 | Barath |
| 5,275,595 A | 1/1994 | Dobak, III |
| 5,458,612 A | 10/1995 | Chin |
| 5,486,208 A | 1/1996 | Ginsburg |
| 5,501,681 A | 3/1996 | Neuwirth et al. |
| 5,545,195 A | 8/1996 | Lennox et al. |
| 5,617,739 A | 4/1997 | Little |
| 5,624,392 A | 4/1997 | Saab |
| 5,644,502 A | 7/1997 | Little |
| 5,733,280 A | 3/1998 | Avitall |
| 5,868,735 A | 2/1999 | Lafontaine |
| 5,902,299 A | 5/1999 | Jayaraman |
| 6,283,959 B1 | 9/2001 | Lalonde et al. |
| 6,300,029 B1 | 10/2001 | Rokutanzono |
| 6,355,029 B1 | 3/2002 | Joye et al. |
| 6,428,534 B1 | 8/2002 | Joye et al. |
| 6,505,629 B1 * | 1/2003 | Mikus et al. .......... 128/898 |
| 6,551,274 B2 | 4/2003 | Heiner |
| 6,575,966 B2 | 6/2003 | Lane et al. |
| 6,648,878 B2 | 11/2003 | Lafontaine |
| 6,786,901 B2 | 9/2004 | Joye et al. |
| 6,974,463 B2 | 12/2005 | Magers et al. |
| 6,989,009 B2 | 1/2006 | Lafontaine |
| 7,402,140 B2 | 7/2008 | Spero et al. |
| 2004/0199229 A1 | 10/2004 | Lasheras |
| 2005/0038421 A1 | 2/2005 | Joye et al. |

FOREIGN PATENT DOCUMENTS

| | | |
|---|---|---|
| WO | 03/061496 A1 | 7/2003 |
| WO | 2004/075949 A2 | 9/2004 |
| WO | 2004/080280 A2 | 9/2004 |
| WO | 2004/108207 A2 | 12/2004 |

* cited by examiner

EFFICIENT CONTROLLED CRYOGENIC FLUID DELIVERY INTO A BALLOON CATHETER AND OTHER TREATMENT DEVICES

CROSS-REFERENCE TO RELATED APPLICATIONS

This application is a continuation application of Ser. No. 11/013,937, filed Dec. 15, 2004, the contents of which is hereby incorporated by reference.

BACKGROUND OF THE INVENTION

The present invention relates generally to apparatus and methods for treatment of tissues using cooling and/or balloon inflation. In many embodiments, the invention provides systems, devices, and methods for cryogenically treating a patient's vasculature or other tissues by cooling the tissues to a temperature in a target temperature range, with cooling fluid pressure and/or the temperature control often being enhanced by measuring one or more characteristics of a cooling fluid flow control valve. Some embodiments may effect controlled inflation of tissue treating balloons with vaporizing and/or gaseous inflation fluids with or without therapeutic tissue cooling.

A number of percutaneous intravascular procedures have been developed for treating atherosclerotic disease in a patient's vasculature. The most successful of these treatments is percutaneous transluminal angioplasty (PTA). PTA employs a catheter having an expansible distal end, usually in the form of an inflatable balloon, to dilate a stenotic region in the vasculature to restore adequate blood flow beyond the stenosis. Other procedures for opening stenotic regions include directional atherectomy, rotational atherectomy, laser angioplasty, stents and the like. While these procedures, particularly PTA and stenting, have gained wide acceptance, they continue to suffer from the subsequent occurrence of restenosis.

Restenosis refers to the re-narrowing of an artery following an initially successful angioplasty or other primary treatment. Restenosis typically occurs within weeks or months of the primary procedure, and may affect up to 50% of all angioplasty patients to some extent. Restenosis results at least in part from smooth muscle cell proliferation in response to the injury caused by the primary treatment. This cell proliferation is referred to as "hyperplasia." Blood vessels in which significant restenosis occurs will typically require further treatment.

A number of strategies have been proposed to treat hyperplasia and reduce restenosis. Previously proposed strategies include prolonged balloon inflation, treatment of the blood vessel with a heated balloon, treatment of the blood vessel with radiation, the administration of anti-thrombotic drugs following the primary treatment, stenting of the region following the primary treatment, the use of drug-eluting stents, and the like. While these proposals have enjoyed varying levels of success, these procedures have not proven to be entirely successful in avoiding all occurrences of restenosis and hyperplasia in all locations, and the costs for implementing many can be excessive for many patients.

It has recently been proposed to prevent or slow reclosure of a lesion following angioplasty in the coronary and/or peripheral vasculature by remodeling the lesion using a combination of dilation and cryogenic cooling. U.S. Pat. No. 6,300,029, the full disclosure of which is incorporated herein by reference, describes a structure and method for inhibiting restenosis using a cryogenically cooled balloon U.S. patent application Ser. No. 10/455,253, filed on Jun. 4, 2003, the full disclosure of which is also incorporated herein by reference, describes improved structures and methods for cryogenically cooling tissues in which a cooled balloon is controllably inflated to one or more intermediate pressures between a non-inflated configuration and a fully inflated, vessel dilating configuration. While these cooled therapies show great promise for endovascular use, the described structures and methods for carrying out endovascular cryogenic cooling would benefit from still further improvements. In particular, work in connection with the present invention indicates that accurate control over balloon inflation pressure, balloon temperature, and the process of going from an uninflated balloon configuration to an inflated cooling balloon configuration may not always provide a desired level of control over an inflation rate while making efficient use cryogenic cooling fluid.

For these reasons, it would be desirable to provide improved devices, systems, and methods for cryogenic cooling of blood vessels and other body lumens. In general, new and enhanced techniques for controlling pressures and temperatures of cryogenic treatments would be beneficial, especially if these improvements did not significantly increase the cost and/or complexity while providing more efficient use of cooling fluids. It would be particularly desirable if these improved devices, systems, and methods were capable of delivering treatment in a very controlled manner so as to limit injury of tissues during endovascular cryogenic balloon inflation.

BRIEF SUMMARY OF THE INVENTION

The present invention provides improved devices, systems, and methods for controllably dilating and/or cooling blood vessels and other body tissues. When used for treating blood vessels, embodiments of the invention will often include a balloon that is inflated by cryogenic cooling fluids so as to cool a surrounding vessel wall for treatment of atherosclerotic or other diseases. Cooling of the balloon may be effected by a change in phase of a cryogenic fluid within the balloon, typically a change from a liquid phase to a gas phase. Treatment pressure and/or temperature profiles over time can be provided while limiting venting or wasting of cryogenic cooling fluid without having to resort to a limited number of "stair-step" increases in pressure. In some embodiments, controlled balloon inflation for dilation or the like may be effected at least in part by a gas inflation, with or without therapeutic cooling.

Work in connection with the invention has determined that the quantity of cryogenic cooling fluid vented from a controlled-temperature and/or pressure treatment probe may be decreased, and/or the control over temperature and/or pressure in such probes may be enhanced by a surprising amount by making use of the measured response of the individual flow control components (particularly solenoid valves) along the cryogenic cooling fluid paths, rather than simply relying on the standard capabilities of the type of components used. For example, rather than employing a minimum pulse width that reliably opens valves of a given type, or even a pulse width that is sufficient to open valves of a given manufacturing batch, a command pulse width will often be measured by determining the least pulse width that can be transmitted to an individual solenoid valve to cause that valve to release significant cryogenic cooling fluid. That pulse width can be measured in the treatment setting using the specific battery that will power the solenoid valve during treatment, and will often allow smaller discrete quantities of cryogenic cooling fluids to be released than can generally be produced using known techniques. A treatment protocol may be determined from the measured pulse width, the protocol optionally employing repeated applications of the measured minimum pulse width.

In a first aspect, the invention provides a method for cryogenic cooling of a target tissue of an individual patient. The method comprises positioning a heat transfer surface with a probe system in thermal communication with the target tissue. A valve performance characteristic of an individual valve of the probe system is measured, and a treatment protocol is determined using the measured valve characteristic. The treatment protocol comprises actuating the valve. The treatment protocol is implemented by actuating the valve to allow cryogenic cooling fluid to flow in thermal contact with the treatment surface so that at least a portion of the cooling fluid vaporizes to cool the tissue.

The treatment protocol will often be performed for the individual patient in a particular treatment setting, and the valve performance characteristic may be measured in that particular treatment setting. For example, when the patient is to be treated in a hospital room, the valve performance characteristic may also be measured in that hospital room, often just prior to treatment of the patient. This can facilitate duplicating the conditions of the treatment, for example, using the same system components, at the same ambient temperature and pressure, and the like.

The valve performance characteristic will often be measured using a controller of the probe system, the controller of the probe system also implementing the treatment protocol. Preferably, the controller will be included in a hand-held housing of the probe system with a receptacle for a cryogenic cooling fluid canister, a controller input, a controller output display, and/or the like. The valve performance characteristic will often be measured using a battery of the probe system, and the battery also energizes an actuator of the valve during the treatment. The individual valve may be disposed of after treating the patient so as to inhibit use of that individual valve for more than one person.

The valve will often comprise a solenoid valve, and the valve performance characteristic may be measured by determining a command pulse width for actuating the valve. The command pulse width may be measured by sequentially assessing candidate pulse widths and monitoring cooling fluid flow within the probe system. The sequential pulse widths may be assessed in order from shorter pulse widths to longer pulse widths, the command pulse width often being determined by comparing a pressure along a cooling fluid flow path downstream of the valve to a threshold pressure.

The command pulse width can be measured using a controller of the probe system, with the controller of the probe system also implementing the treatment protocol by: a) transmitting a command pulse having the command pulse width to the valve; b) measuring a cooling fluid pressure adjacent to or downstream of the heat transfer surface along the fluid flow path in response to the preceding command pulse; c) comparing the measured pressure to a target pressure; d) repeating a)-c) in response to the measured pressure being less than the target pressure; and e) ending a)-d) in response to the measured pressure being greater than the target pressure. The target pressure can be changed as a function of time. For example, the target pressure may increase linearly as a function of increasing time, thereby providing a smooth and gradual increase in the inflation pressure. In some embodiments, the pressure may increase at a first rate during a first portion of the inflation cycle, and may then increase at a second rate during a second portion of the inflation cycle. For example, a relatively low initial inflation rate of less than 5 psi/sec. may be used to gradually open a balloon from a small profile configuration to a deployed profile configuration, and may then be followed by an inflation rate of over 5 psi/sec. to avoid excessive inflation times to dilation pressures. Such smooth and gradual inflation may avoid rapid movement or snapping of the balloon wall against adjacent tissues, and the like Still further treatment pressure and/or temperature profiles are possible, with temperature and pressure of cryogenic fluids often being coupled by the relationship between vaporization temperature and pressure in a vaporization chamber in thermal contact with a treatment surface. Along with the ability to provide selected treatment temperatures and/or pressures, controlled rates of change of these parameters may be provided, differing dwell times at differing temperatures or pressures, repeated cycling of temperature/pressure excursions, and the like may also be employed.

The treatment protocol may comprise a plurality of command pulses transmitted to the solenoid valve, with each command pulse having the command pulse width. Each command pulse may release an associated mass of cryogenic cooling fluid along the cooling fluid path. The cooling surface may comprise a balloon, and the target pressure may change so that the balloon gradually changes between an uninflated configuration and a tissue dilating configuration. The command pulse width may be sufficiently short that a majority of the total mass of cooling fluid released by the command pulses vaporizes along the cooling fluid path. Unlike some step-wise changes in cryogenic balloon inflation pressure, the gradual change in pressure may be limited to pressure inflation rates of no more than 100 psi/sec., often being less than 50 psi/sec., and ideally being less than 5 psi/sec. throughout an increase in pressure of at least 5 psi.

The valve will often be assembled with other components of the probe system by a probe system manufacturer. The valve may be among a plurality of valves sharing a common valve model, and may be supplied by the probe system manufacturer by a valve supplier. The command pulse width will often be less than a minimum pulse width for reliably opening the plurality of valves of the valve model The minimum model pulse width may be identified by the probe system manufacturer and/or the valve supplier The command pulse width will often comprise a minimum pulse width to achieve a desired actuation response of the particular valve. It should be noted that the minimum command pulse width measured by the controller and/or applied during treatment need not be the absolute minimum pulse width to open and close the valve. For example, a small safety factor may be added to the minimum measured pulse width. When measuring the minimum pulse width, the controller may scan sequential candidate pulse widths, with the candidate pulse widths increasing by a step size, so that the measured minimum pulse widths may be slightly larger than an absolute minimum pulse width that fails between two candidates. Nonetheless, the command pulse width may be described as a minimum pulse width or minimum delivery pulse width. In either case, this measured valve characteristic of the individual valve may provide control over inflation pressures and/or temperatures with vaporizing cryogenic inflation fluids that is beyond the capability of systems which simply employ a standard pulse width acceptable for all valves of a given type or model.

In another aspect, the invention provides a method for cryogenic cooling of a tissue of an individual patient. The method comprises positioning a heat transfer surface of a probe system in thermal contact with the tissue. A minimum acceptable command pulse width of an individual solenoid valve of the probe system is measured using a controller of the probe system. The tissue is cooled by repeatedly actuating, with the controller of the probe system, the valve according to the minimum command pulse width so as to allow cryogenic cooling fluid to flow in thermal contact with the treatment surface. At least a portion of the cooling fluid vaporizes.

In another aspect, the invention provides a method for treating a target tissue of an individual patient. The method comprises positioning a balloon of a balloon system adjacent to the target tissue and measuring a valve performance characteristic of an individual valve of the balloon system. A treatment protocol is determined using the measured valve characteristic, the treatment protocol comprising actuating the valve The treatment protocol is implemented by actuating the valve to allow fluid to flow into the balloon so that at least a portion of the fluid within the balloon comprises a gas, and so that the gas inflates the balloon.

The balloon will often be used to dilate the target tissue, and the balloon system may, or may not, effect cooling of the target tissue Dilation pressure can be accurate controlled throughout the dilation treatment cycle, and visualization of the balloon may be facilitated by a radiopaque material disposed along the balloon. Surprisingly, such gas inflation may be easier and/or more repeatable than standard liquid and contrast inflation, thereby facilitating angioplasty, stenting, peripheral vessel dilation, and a variety of other balloon system treatments. The valve will often comprise a solenoid valve, and the valve performance characteristic is often measured by determining a minimum command pulse width for actuating the valve At least a portion of the fluid comprises a liquid that vaporizes within the balloon.

In another aspect, the invention provides a system for treatment of a tissue of an individual patient. The system comprises a probe having a fluid path and a treatment surface coupled thereto. The fluid path is couplable to a fluid source. A valve is disposed along the fluid path of the probe, and a sensor is disposed along the fluid path of the probe. A controller is coupled to the valve and to the sensor The controller is configured to measure a characteristic of the valve by actuating the valve and monitoring the cooling fluid with the sensor. The controller is also configured to determine a treatment protocol in response to the measured valve characteristic, and to implement the treatment protocol by actuating the valve so as to cool the tissue.

The valve will often comprise a solenoid valve, and the valve performance characteristic will typically comprise a command pulse width for actuating the valve. The measured command pulse width will often comprise a minimum command pulse width to achieve a desired actuation result. The measured command pulse width need not be the absolute minimum command pulse width to allow release of any cooling fluid, but may be less than a minimum pulse width identified by the valve supplier for reliably opening valves of the same valve model.

A battery may be in electrical communication with the controller, and the controller may be configured to measure the valve performance characteristic and implement actuation of the valve so as to treat the tissue using the battery. The controller may be configured to measure the command pulse width by sequentially assessing candidate pulse widths while monitoring for cooling fluid with the sensor. The sequential candidate pulse widths may be assessed in an order from generally shorter pulse widths to generally longer pulse widths. While some variation in the order may be employed, maintaining the general trend of going from shorter pulse widths to longer pulse widths avoids unnecessary release of cooling fluid when a minimum effective pulse width is to be identified. The sensor may comprise a pressure sensor to indicate cooling fluid flow and/or pressure along the path, and the controller may be configured to determine the command pulse width by comparing the pressure along the cooling fluid path to a threshold pressure.

The controller may be configured to implement the treatment protocol by transmitting a command pulse having the command pulse width to the valve. A cooling fluid pressure adjacent to or downstream of the heat transfer surface may be measured along the fluid flow path, as the cooling fluid may change in response to each preceding command pulse. The measured pressure may be compared to a target pressure, and the command pulse transmitting, measuring, and comparing may be repeated when the measured pressure is less than the target pressure. The transmitting, measuring, comparing, and/or repeating may be ended in response to the measured pressure being greater than the target pressure.

The controller may be configured to change the target pressure as a function of time. Optionally, the treatment protocol may comprise a plurality of command pulses having the command pulse width. Each command pulse may release an associated mass of cryogenic cooling fluid along the cooling fluid path. The cooling surface may optionally comprise a balloon, and the controller may be configured to gradually change the target pressure so that the balloon gradually changes between an uninflated configuration and a tissue dilating configuration. The command pulse width may be sufficiently short that a majority of the total mass of cooling fluid released by the command pulses vaporizes along the cooling fluid path.

DETAILED DESCRIPTION OF THE INVENTION

The present invention generally provides improved devices, systems, and methods for dilating and/or cooling treatments of the luminal wall in body lumens and other tissues of the body. The invention often makes use of a balloon which is inflated by a cooling fluid so as to radially engage a vessel wall (or other surrounding tissue). The cooling fluid will often change from a first phase to a second phase at least in part within the balloon, so that the latent heat of vaporization cools the surrounding tissues. Introduction of suitable cooling fluids is capable of very rapidly expanding the balloon once the cooling fluid begins to boil from a liquid to a gas phase (often occurring soon after the fluid enters the catheter) The invention is capable of providing advantageous control over the balloon inflation process, for example, allowing smooth and gradual changes to the pressure state within the balloon over time. As pressure and temperature are related in cryogenic cooling systems employing vaporization with mixtures of liquid and vapor in thermal contact with the cooling treatment surface, the invention may allow a wide variety of temperature and/or pressure treatment profiles, often without having to resort to significant "stair step" changes so as to avoid excessive venting or waste of cooling fluid. Similar techniques may be employed to inflate balloons at least in part with a gas but without therapeutic cooling.

While the invention will be described below largely in embodiments employing inflatable balloon catheters, alternative probe structures may also take advantage of the efficient cooling fluid control devices, systems, and methods described herein. For example, flexible cryogenic catheters having vaporization chambers which do not expand may find use for controllably forming lesions in cardiac tissue so as to treat arrhythmias and other coronary diseases. Rigid probes having fixed and/or inflatable treatment surfaces may find applications in open or minimally invasive surgery for a wide range of therapies of tissues throughout the body, and/or of specific tissues which would benefit from the applications of controlled pressure and/or temperature profiles to provide controlled cryogenic ablation or other cooled therapies.

Figure 1:
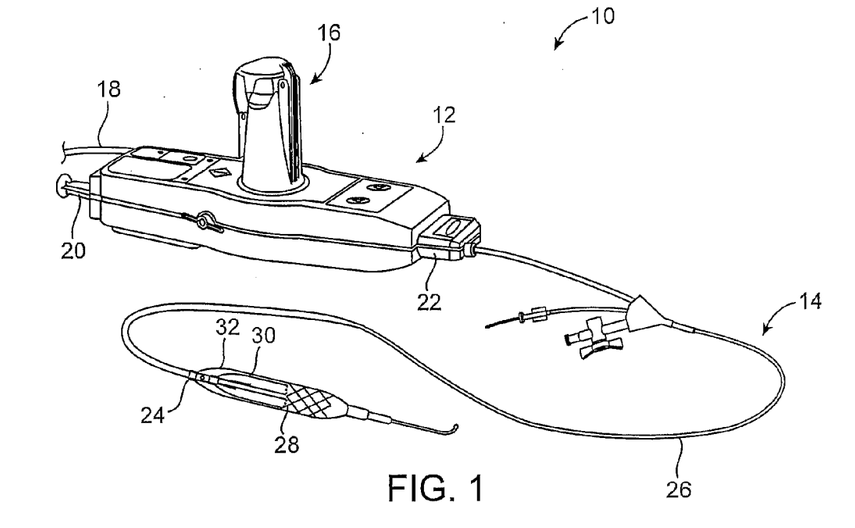
FIG. 1 is a perspective partial cutaway view of a cryogenic balloon catheter system according to the principles of the present invention

Referring now to FIG. 1, a catheter system 10 generally includes a controller/supply unit 12 and a catheter 14. Unit 12 includes a cooling fluid supply 16 along with cooling fluid control system components such as valves, pressure transducers, electronic controller hardware and/or software, and the like. Unit 12 may optionally incorporate user interface capabilities including switches, input keys, a display, and the like. Alternative embodiments may make use of external user interface or data processing structures, and the components of unit 12 may be separated into different housing structures.

The exemplary supply/control unit 12 includes a cable 18 for supplying electrical power from a battery, wall outlet, or other convenient power source. Additionally, a vacuum source 20 is integrated into unit 12, here in the form of a positive displacement pump such as a syringe. A housing of unit 12 has a size, shape, and weight suitable for holding in a single hand during a procedure. Unit 12 is coupled to catheter 14 by interfacing hubs or connectors 22 on the unit and catheter. Unit 12, catheter 14, and the interfacing connectors are more fully described in U.S. Pat. No. 6,648,879 entitled "Improved Safety Cryotherapy Catheter," the full disclosure of which is incorporated herein by reference.

Catheter 14 generally has a proximal end adjacent connector 22, a distal end 24, and an elongate catheter body 26 extending therebetween. A balloon 28 is disposed adjacent distal end 24 of catheter body 26. In the exemplary embodiment, balloon 28 comprises an inner balloon 30 and an outer balloon 32 (see FIG. 2). By monitoring a vacuum applied between the first and second balloons, and by shutting off the cooling fluid flow if the vacuum deteriorates, containment of both the first and second balloons can be effectively monitored and release of cooling liquid or gas within the vasculature can be inhibited.

During a cryogenically cooled balloon inflation, the inflation fluid may be maintained in a canister within unit 12 at a high pressure of over 650 psi, typically at between 850 and 950 psi. Use of a small sealed canister having a small volume provides a convenient single-use system which can limit overtreatment by exhaustion of the cooling fluid. Nitrous oxide canisters having volumes between 10 cc and 20 cc may contain from about 8 gms to about 25 gms of cooling fluid to provide a very safe, effective cooling and inflation media for the balloon catheter system 10. However, balloon inflation rates when these high-pressure canisters are coupled to balloon catheter system 10 may be excessive, often being less than 0.1 seconds. Balloon inflations at these high rates can cause excessive damage to the vessel in the treatment area, and may result in higher dissection rates, higher restenosis rates, and the like.

A variety of control methodologies may be employed to reduce the balloon inflation rate, including any of those more fully described in U.S. patent application Ser. No. 10/455, 253, filed on Jun. 4, 2003, and entitled "Controllable Pressure Cryogenic Balloon Treatment System and Method," the full disclosure of which is also incorporated herein by reference. As noted in that references, significant variations between the catheters, the volume and diameter of the cooling fluid inflow lumens to the balloons, the temperature of the tubing transmitting the cooling fluid, the manifold coupling the supply canister to the catheter body, and other physical differences can significantly alter the temperature and/or gas/liquid mix of the nitrous oxide fluid entering the catheter. This can complicate pressure control algorithms, making it difficult to produce a uniform response in the widely varying catheters which might be selected Furthermore, the response time of the entire cooling fluid system when measuring exhaust flow from the catheter body may make it difficult to rely on a simple feedback loop so as to produce, for example, gradual pressure changes when using any of a range of catheters Unit 12 may be selectively coupled to any of a plurality of selectable balloon catheters, which will often have catheter bodies, balloons, and/or other components with significantly differing characteristics. More specifically, an exemplary set of alternatively selectable catheters may include catheter body lengths of 80, 120, and 135 cm, along with balloon lengths of 2, 4, 6, and 8 cm. Some or all of the combinations of body lengths and balloon lengths may be available in catheters having balloons with diameters of 2.5, 3.0, 3.5, 4, 5, 6, 7, and 8 mm. An exemplary set includes 48 catheters having differing flow characteristics, which may result from additional differences between the catheter structures. For example, along with differing catheter lengths, balloon lengths, and balloon diameters, the orifice length for cooling of fluid entering the balloon may differ among the differing catheters (often as a function of balloon length, with longer balloons having shorter orifices so that the flow rate of cooling fluid will be sufficient to cool the entire balloon surface). As these differing characteristics will significantly impact the flow characteristics of the cooling fluid from unit 12, a control methodology providing a controlled inflation rate for any of the selected balloon catheters when coupled to unit 12, is desirable.

Figures 2, 3:
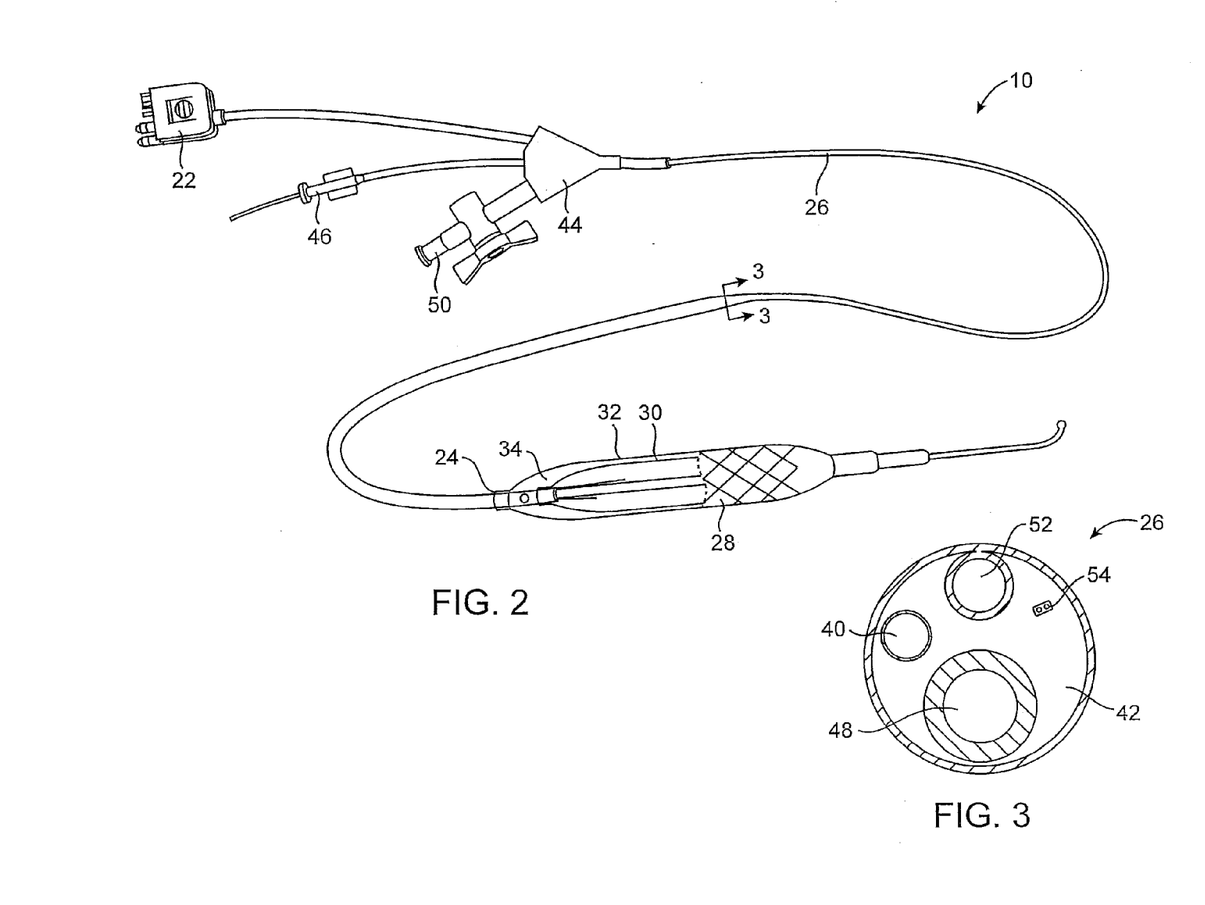
FIG. 2 is a partial cutaway view of a balloon catheter of the system of FIG 1.
FIG. 3 is a cross-sectional view through the balloon catheter of FIG. 3 taken along lines 3-3.

Referring now to FIGS. 2 and 3, a variety of the structures of catheter 10 are shown in more detail. Catheter body 26 includes a cooling fluid supply lumen 40 and an exhaust lumen 42 extending the proximal and distal ends of the catheter body. The first and second balloons 30, 32 maybe integral extensions of the catheter body, or maybe separately formed and attached thereto. The balloon may be formed from the same or different material as the catheter body and may be attached to the catheter body by adhesives, heat welding, or the like. Catheter body 26 may comprise a variety of polymer materials, including polyethylenes, polyimides, nylons, polyesters, and/or copolymers and derivatives thereof Balloon 30, 32 may comprise elastic and/or inelastic structures, and may comprise material such as nylon, polyethyleneterephathalate (PET), urethane, latex, silicone, polyethylene, high strength polymers such as PEBAX™, and/or the like. Balloons 30, 32 may be formed from different materials, for example, the first balloon comprising a high-strength material such as PET, while the second balloon comprising a highly durable material such as polyethylene. Balloon 28 will typically have a length of at least 1 cm, preferably being in a range from about 1.5 cm to 10 cm, and may have diameters in a range from 1.5 mm to about 10 mm.

A thermal barrier may be disposed within vacuum space 34, the thermal barrier comprising or maintaining a gap between the balloons. Suitable thermal barriers may comprise woven, braided, helically wound, or knotted fibers such as polyester materials commercially available from SAATITECH of Summers, N.Y. as the SAATIFIL™ polyester, PES 38/31M. A radiopaque marker may also be disposed on the polyester layer, or otherwise between the first and second balloons so as to facilitate imaging. A wide variety of alternative structures are also possible.

Still referring to FIGS. 2 and 3, a hub 44 along catheter body 26 may couple a guidewire port 46 to a guidewire lumen 48 of the catheter body. A balloon deflation port 50 is coupled to exhaust lumen 42 so as to facilitate deflation of the balloon after completion of a procedure. At least one rupture disk may disposed between the inner surface of the inner balloon and the vacuum space so as to shut down the system prior to a balloon burst. Vacuum space 34 may be coupled to hub 22 by vacuum lumen 52, while wire 54 couple sensors of the balloon to unit 12.

Figure 4:
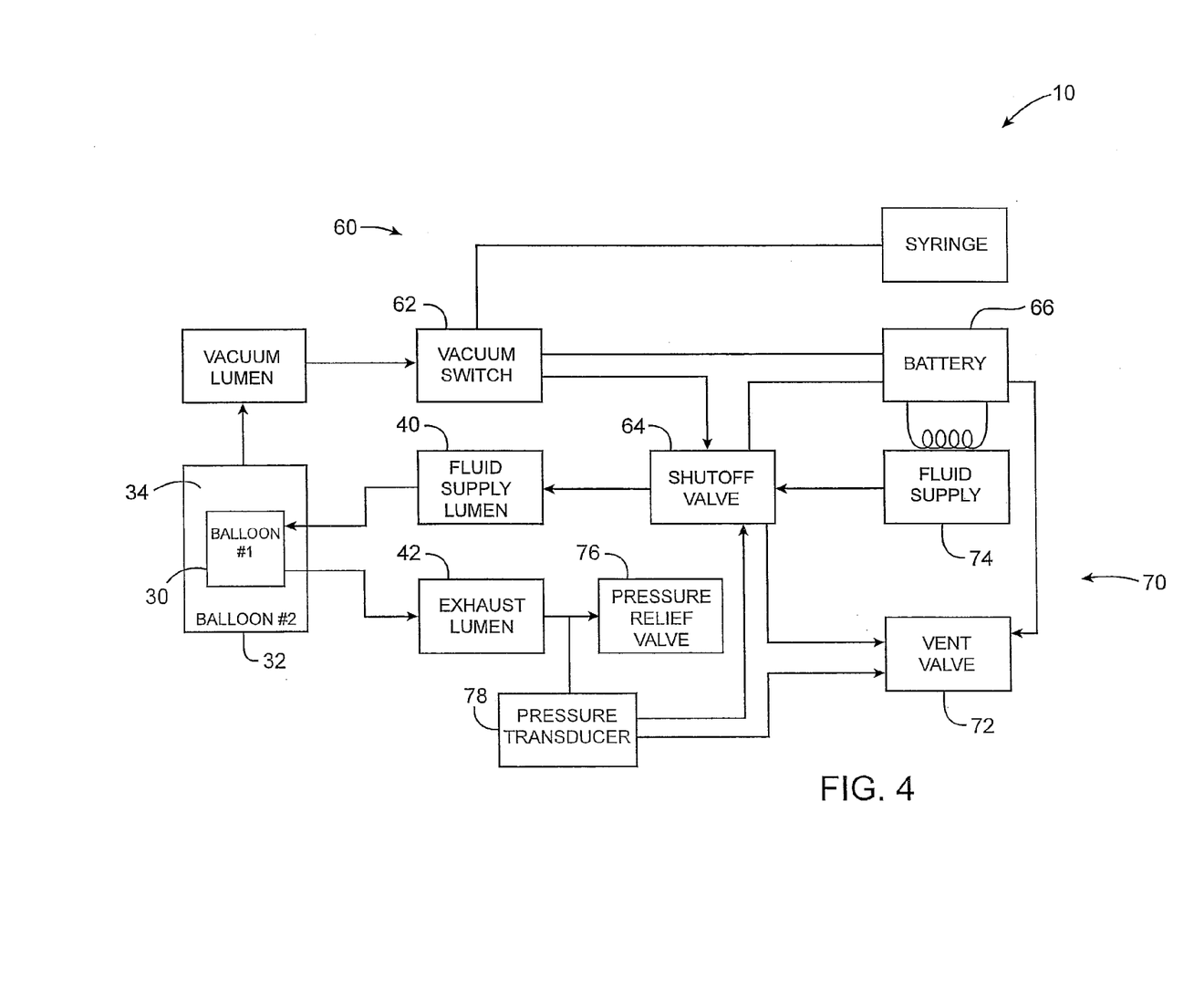
FIG. 4 is a functional block diagram illustrating components of the balloon catheter system of FIG. 1.

FIG. 4 illustrates a functional flow diagram of some of the fluid path and control components of system 10. A fluid shut-off portion 60 of system 10 generally includes a vacuum switch 62 connected to a shut-off valve 64 by a circuit, the circuit being powered by a battery 66. The switch 62 may remain closed only when a predetermined level of vacuum is detected. Alternatively, the circuit may be arranged so that the switch is open only when the predetermined vacuum is present, with the shut-off valve 64 being opened when the switch is open. The vacuum is reduced when there is a breach in the catheter body, inner balloon, and/or outer balloon, allowing cryogenic fluid or blood to enter the vacuum lumen or vacuum space.

In a pressure control portion 70 of the system, fluid flows along a cooling fluid path from a fluid supply 74 (such as a nitrous oxide canister) through a solenoid delivery valve 64. When valve 64 is opened, fluid is allowed to advance along fluid supply lumen 40 to balloon 30, where at least a portion of the cooling fluid changes phase from a liquid to a gas Some portion of the fluid may also change from a liquid to a gas prior to entry of balloon 30 and/or after the balloon is exhausted from balloon 30 into exhaust lumen 42 A pressure relief valve 76 controls release of the exhaust, typically to the surrounding environment. In alternative systems, the exhaust may be released to a vacuum source, a waste chamber, a recycling system, or the like. Relief valve 76 controls the back pressure in exhaust lumen 42 and balloon 30.

When valve 64 is opened, the cooling fluid from fluid supply 74 is also allowed to advance to a vent valve 72. Then valve 72 (and other structures of the cooling fluid control portion 70) are coupled to battery 66. The coupling circuitry will often comprise a timer to establish a valve cycle time. When vent valve 72 is open, cooling fluid from the fluid supply and/or fluid supply lumen is vented, significantly limiting the flow of cooling fluid into balloon 30.

Figure 5:
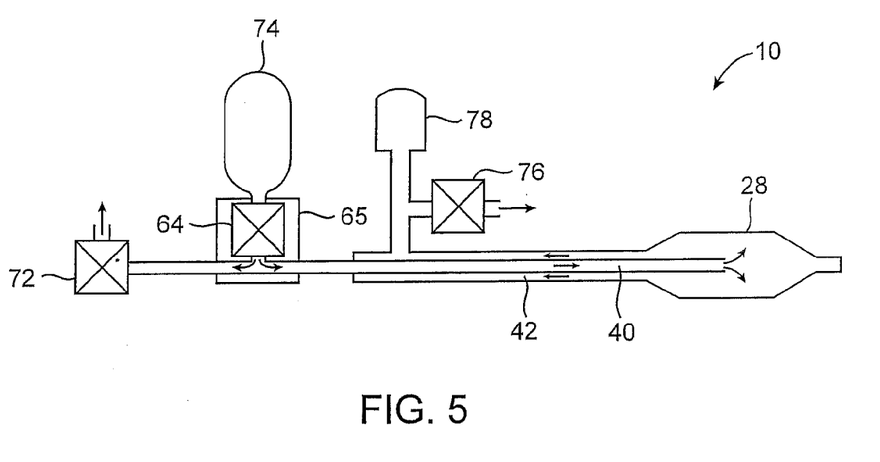
FIG. 5 is a schematic illustrating components disposed along the cooling fluid flow path of the system of FIG. 1

As explained in detailed in U.S. patent application Ser. No. 10/455,253, intermediate balloon configuration (between uninflated and fully inflated) and/or stair-step inflation pressures changes may be implemented using a venting and/or shut-off valve cycle regimen selected in response to a measured pressure from transducer 78. Specifically, an initial or calibration cooling fluid flow may be introduced in the fluid supply 40 by opening and closing valve 64. By measuring the pressure at transducer 78, this allows the controller to determine at least some of the cooling fluid flow path characteristics for the system. In the exemplary embodiment, a valve cycle time for the vent valve and/or shut-off valve are determined in response to a pressure of the exhaust measured by pressure transducer 78 so as to accommodate the system response given the length of the catheter body, balloon size, etc. Components of system 10 along the cooling fluid flow path are illustrated in FIG. 5.

Figure 6:
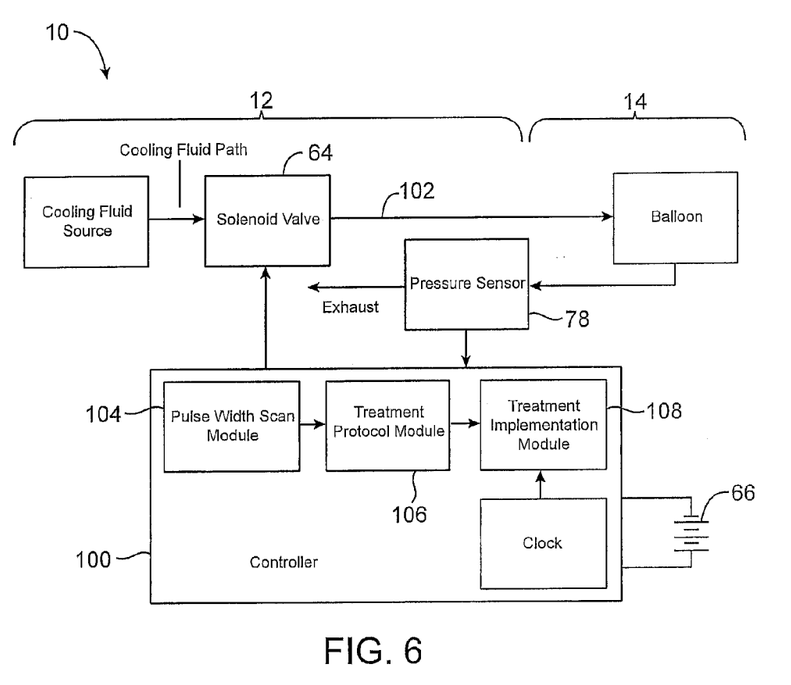
FIG. 6 schematically illustrates components of a controller for controlling inflation pressure and/or temperature over time, and shows interactions between the controller and components of the cooling fluid path.

Referring now to FIG. 6, interaction between the controller 100 and components along a cooling fluid flow path 102 are schematically illustrated. Cooling fluid flow is controlled at least in part by a solenoid valve 64 along cooling fluid flow path 102. Pressure transducer 78 acts as a pressure sensor so as to monitor cooling fluid flow along the cooling fluid path.

Solenoid valve 64 is included in unit 12, and is assembled with the other components of the unit by a probe system manufacturer. Solenoid valve 64 may optionally be reused along with unit 12, while catheter 14 is disposable and intended for use with only a single patient. In other embodiments, the valve may comprise a structure of catheter 14, so that the valve is used for only a single specific patient. In either case, the solenoid valve will often have an associated valve type, such as a model number, name, or the like. The valve may also have an associated batch number, or the like. A plurality of valves of the same type, model, name, number, and/or batch number will often be supplied by a valve supplier (such as a valve manufacturer or intermediate valve sales organization) to the probe system manufacturer.

Valve suppliers will typically provide information regarding the characteristics of the valves provided to the probe system manufacturer, with the information often including a specified minimum pulse width for actuating the solenoid valve This information will often accurately identify a pulse width which is sufficient to reliably actuate the valves of the type (or the like) when the specified valve actuation potential is applied. However, the individual valves of that type will often be capable of opening and closing in response to pulse widths which are significantly less than the type of model information specified by the valve supplier. In fact, the valves may be capable of metering extremely small amounts of cooling fluids. Achieving the desired control precision to smoothly and gradually change pressure within a dilation balloon (for example) is significantly enhanced by operating the valve near the limit of the individual valve's capability. So as to open and close the valve near its individual capability and minimize flow with each pulse, an electrical pulse width which varies with the individual valve, the battery voltage, the ambient temperature, and/or the like is desirable.

So as to open and close the valve near its individual capabilities, an electrical pulse width which achieves a minimum valve response will often be measured for that specific valve. Due to manufacturing variations in the valve, conditions under which the valve is actuated, and the like, the individual valve performance and minimum delivery pulse width may differ significantly from the specified valve characteristics.

So as to take advantage of the individual valve capabilities, controller 100 generally includes modules for scanning pulse widths 104, establishing a treatment protocol 106, and implementing the treatment protocol 108. Controller 100 will generally comprise software and/or hardware for implementing a series of method steps, with the exemplary modules comprising reprogrammable hardware programmed with machine readable code. The exemplary controller comprises a Microchip Pic™ processor, and is programmed in the C computer language.

In general terms, pulse width scan module 104 determines a command pulse width which provides a desired response from the valve, with the pulse width typically comprising a "minimum" pulse width to produce the desired result. It should be noted that the pulse width need not necessarily be the absolute minimum pulse width, as a safety factor may be added to or multiplied by the scan results, and as the scan itself may comprise a simple trial of candidate individual pulse widths which increase by an increment (so that some intermediate pulse width between two candidates may also be capable of providing the desired result).

Treatment protocol module 106 generally establishes a treatment protocol in response to the pulse width identified by the pulse width scan module 104. In the exemplary embodiment, the treatment protocol module may be as simple as setting a command pulse width variable equal to the smallest candidate pulse width which produces a desired result. Alternative embodiments may modify the selected candidate pulse width, or may redefine the treatment protocol so as to make appropriate use of the specific characteristics of the solenoid valve 64 included in system 10.

The treatment implementation module 108 will generally effect a desired cryogenic tissue treatment, often including one or more tissue treatment temperatures, one or more tissue cooling rates, one or more dwell times at a treatment temperature, and/or the like. The treatment temperatures and temperature change rates may be defined as specific target treatment temperatures or rates, or by target ranges So as to effect a controlled change in temperature or pressure within a desired rate range, treatment implementation module 108 will often receive input from a clock of controller 100. Treatment implementation module 108 will often direct electrical potential from battery 66 to solenoid valve 64 according to the measured pulse width or other valve performance characteristic, with at least one of the pulse width scan module 104 and treatment implementation module 108 making use of feedback from pressure sensor 78 in determining the valve characteristics and/or implementing the treatment.

Figure 7:
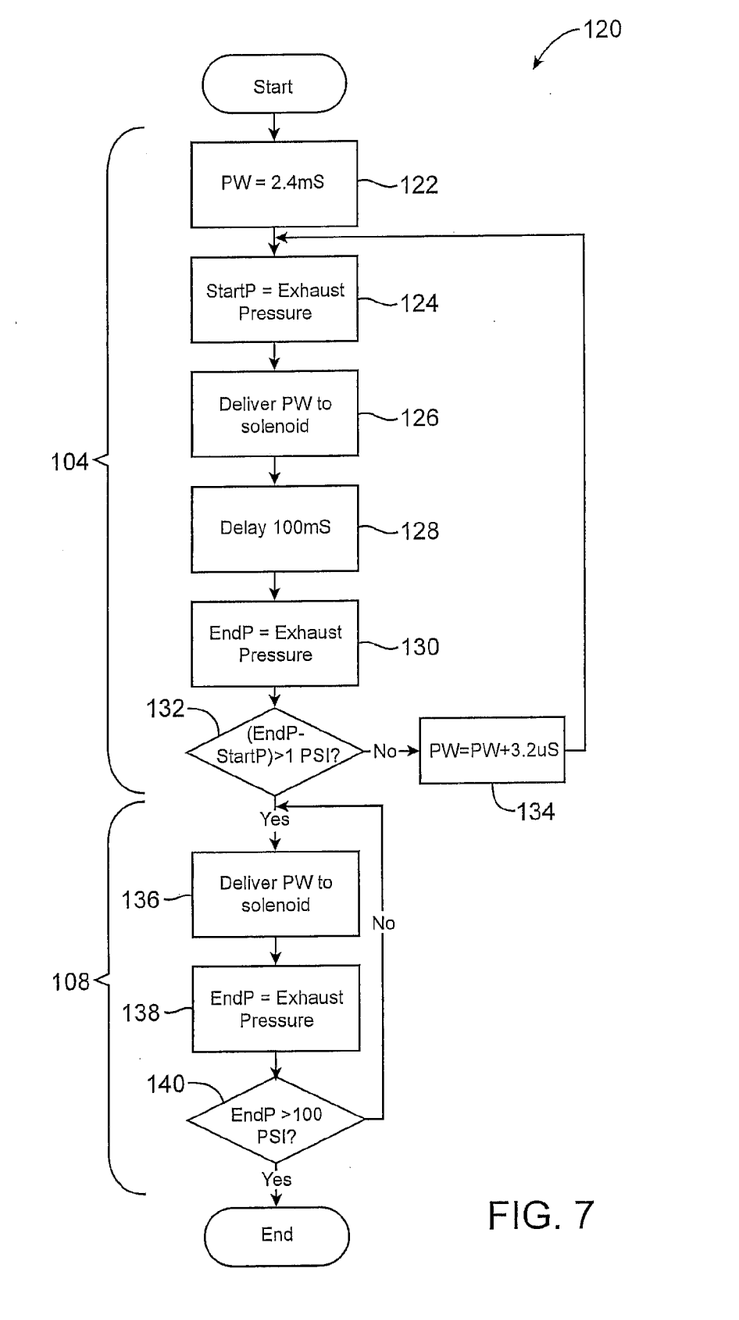
FIG. 7 is a flow chart schematically illustrating a method for measuring a minimal pulse width for a solenoid valve along the cooling fluid path in the system of FIG. 1, along with a simple protocol to provide a desired treatment pressure.

Referring now to FIG. 7, an exemplary method for scanning valve pulse widths and implementing a single specific inflation pressure is illustrated in more detail. Method 120 sets a first candidate pulse width PW at an initial value 122 and measures an exhaust pressure at pressure sensor 78 in box 124. The initial pulse width will typically be less than 0.1 seconds, often being less than 30 mS, in many cases, less than 10 mS, and ideally less than 3 mS. The established pulse width is delivered to the solenoid 126, after which an appropriate delay 128 is implemented to allow the system to register an exhaust pressure 130 resulting from the commanded pulse. The end pressure will typically also be measured by pressure sensor 78, and the ending pressure is compared to the starting pressure to determine if a threshold change in pressure or other cooling fluid response has been produced in box 132, the threshold pressure change often being less then 5 psi, ideally being less than 2 psi.

If the prior commanded pulse and did not produce a change in pressure which is greater than the threshold, the pulse width is increased by an increment 134 and the exhaust or pressure is again measured 124. The pulse width increment may be less than 10 mS, often being less than 1.0 mS. The new pulse width command is directed to the solenoid 126, and the system response is again measured against the threshold. The pulse width is increased repeatedly until the threshold response is achieved.

Scanning the candidate pulse widths from generally shorter candidate pulse widths to generally longer candidate pulse widths avoids excessive release of cooling fluid along the cooling fluid flow path during the pulse width scan implemented by scan module 104. The order need not be absolute, as (for example) large pulse width increments may initially be employed to narrow the scan range, with subsequent finer scan increments. Nonetheless, by having the majority of pulses in the scan sequence be longer than the majority of prior pulses the total use of cooling fluid in the scan may be limited.

Once the minimum delivery pulse width to produce a desired result has been identified, the treatment protocol can be established using that identified pulse width (or some other command pulse width derived therefrom). In the method 120 illustrated in FIG. 7, the treatment protocol is established by merely setting a command pulse width equal to the selected candidate pulse width PW. Other embodiments may modify the identified candidate pulse width by adding or multiplying the identified candidate by a safety factor, or the like.

Method 120 includes a portion implemented by treatment implementation module 108. This portion makes use of the command pulse width derived from the pulse width scan by transmitting the pulse width to the solenoid valve in box 136. The exhaust pressure is measured by pressure sensor 78 in box 138, and the exhaust pressure is compared to a target pressure 140. During at least a portion of the treatment protocol, the target pressure may comprise a fixed pressure. In other portions of the treatment protocol, the target pressure may be a function of time. Regardless, if the target pressure has not yet been provided, method 120 involves transmitting the pulse width once again to the solenoid in box 136 and measuring the exhaust pressure. This is repeated until the target pressure has been provided.

While the flow chart illustrating method 120 includes significant detail, further refinements will often be included. For example, sufficient delay may be implemented between delivery of the pulse width in box 136 and measurement of the exhaust pressure in box 138 so as to allow the probe system pressure to respond appropriately. Additionally, the treatment will typically not end once the target pressure is produced in box 140. Instead, some pressure decay delay time may be provided, or the exhaust pressure may be monitored until it drops below the target pressure. After the pressure has decayed below a pressure in the target pressure range, the command pulse width may again be directed to the solenoid in box 136, and so on until the target pressure is again achieved. Alternatively, the solenoid valve and/or vent valve may be cycled open and closed periodically, optionally using methods similar to those described in U.S. patent application Ser. No. 10/455,253.

Figure 8:
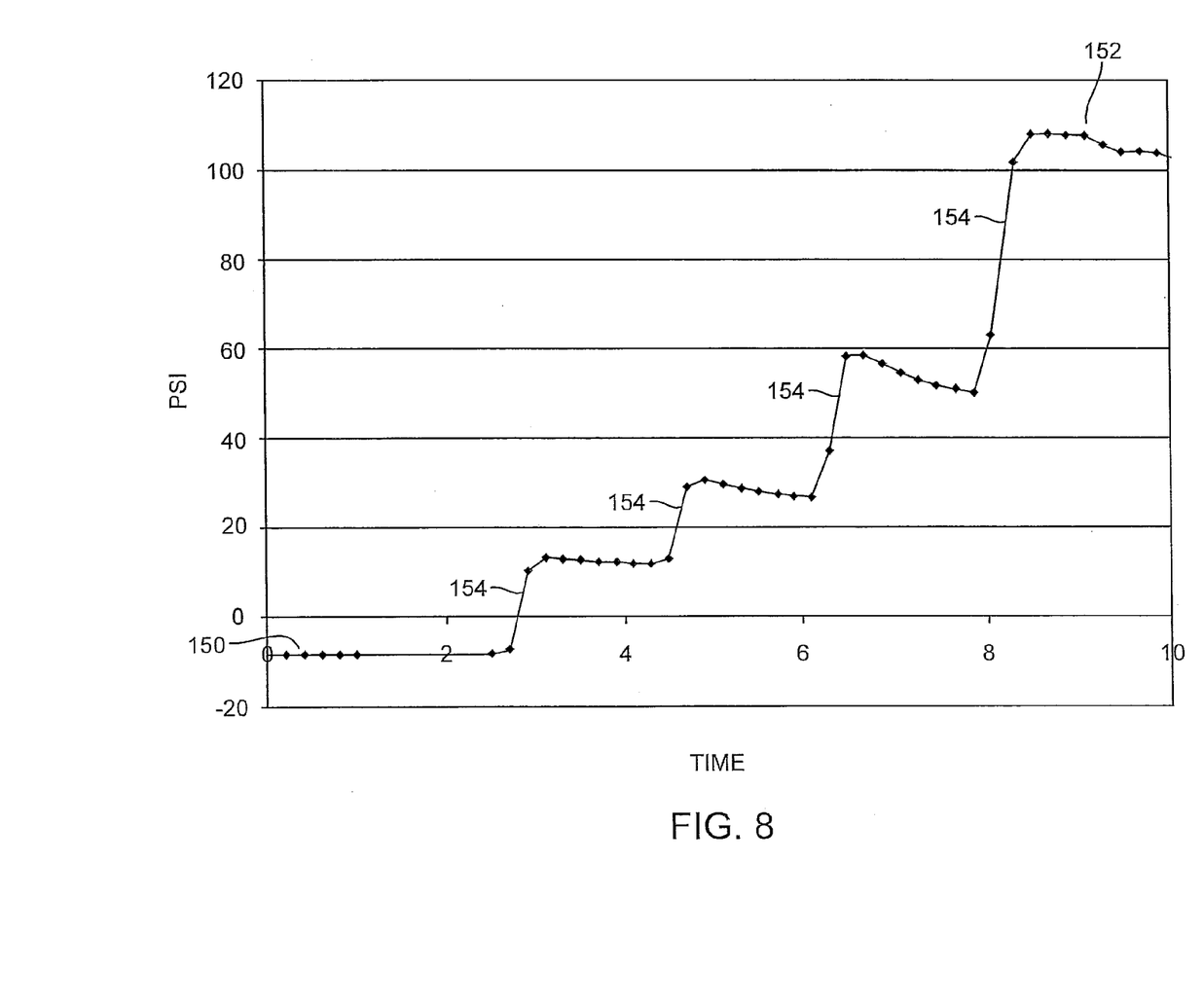
FIG. 8 illustrates a "stair-step" pressure increase from an uninflated balloon configuration to a blood vessel dilating inflated balloon configuration.

Referring now to FIG. 8, a step-wise inflation of a cryogenic balloon catheter is shown graphically with inflation pressure in psi over time in seconds. While the balloon passes through a plurality of intermediate configurations between an uninflated configuration 150 and an inflated configuration 152, the balloon inflation rates 154 exceed 50 psi/sec. While such step-wise inflation may optionally be effected by system 10, more gradual inflation, particularly when initially expanding the balloon from the uninflated configuration 150, would be advantageous. Note that pressures may initially be less than zero as a vacuum can be drawn in the balloon to maintain a small profile for insertion and positioning.

Figure 9:
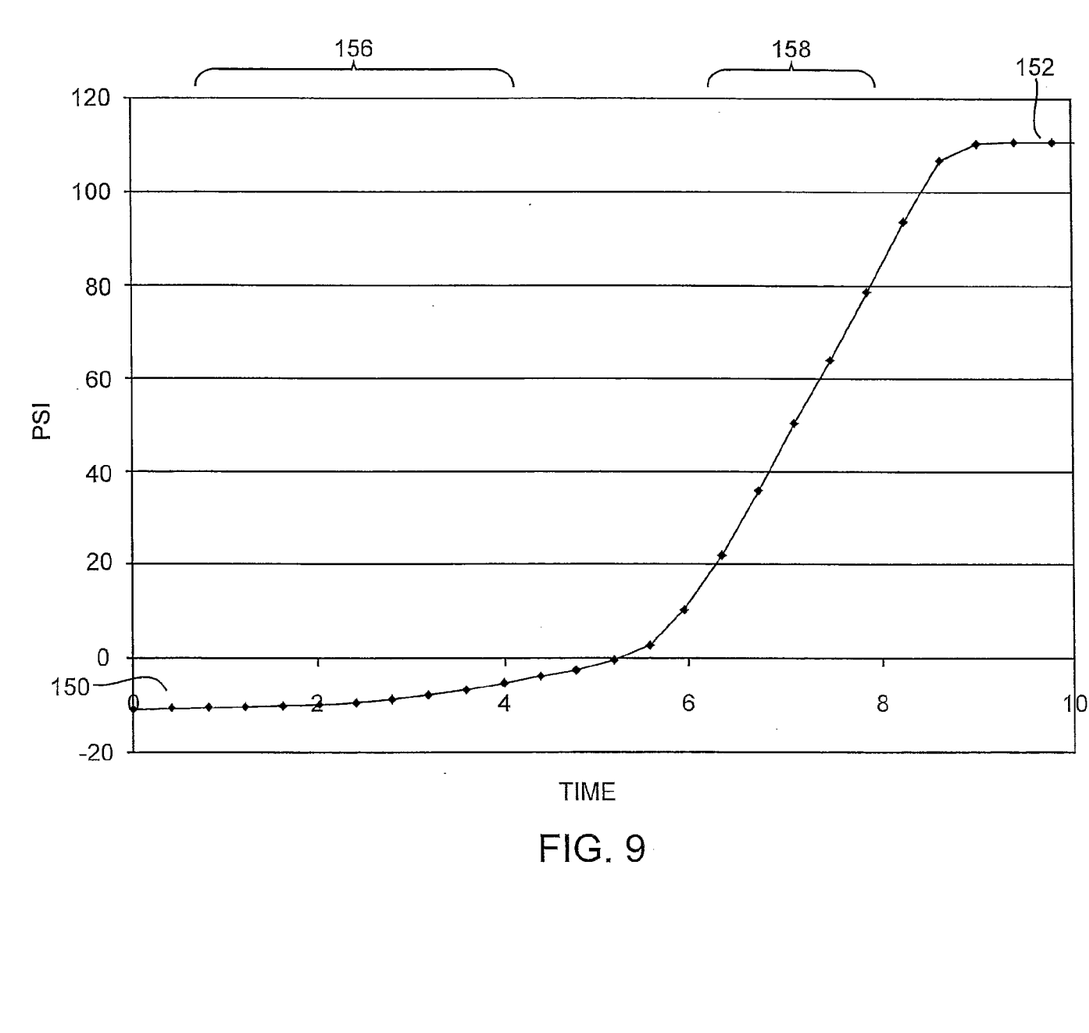
FIG. 9 illustrates a smooth and gradual inflation of a cooled balloon from an uninflated configuration to a blood vessel dilating configuration using the system of FIG. 1.

Referring now to FIG. 9, an alternative inflation from uninflated configuration 150 to inflated configuration 152 includes smooth and gradual changes in pressure at much lower pressure change rates.

An initial portion 156 of the inflation includes a rate of change in pressure limited to pressure less than 5 psi/sec, gradually moving the balloon walls radially outwardly from uninflated configuration 150 and into engagement with the surrounding vessel wall. Once the balloon has been inflated sufficiently (such as to an inflation pressure of greater than one atmosphere) a somewhat more rapid pressure change rate may be implemented in another portion 158 of the inflation cycle. Throughout this inflation, use of the minimum pulse width for the specific solenoid valve of the cryogenic probe system.

Figure 10A:
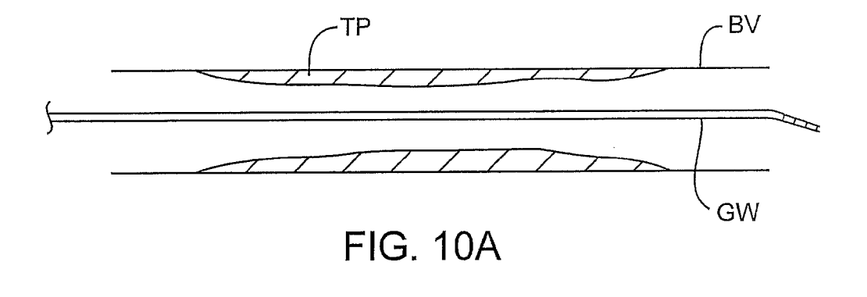
FIGS. 10A-10C are cross-sectional drawings taken through a blood vessel to schematically illustrate a method for treatment using the system of FIG. 1.
Figure 10B:
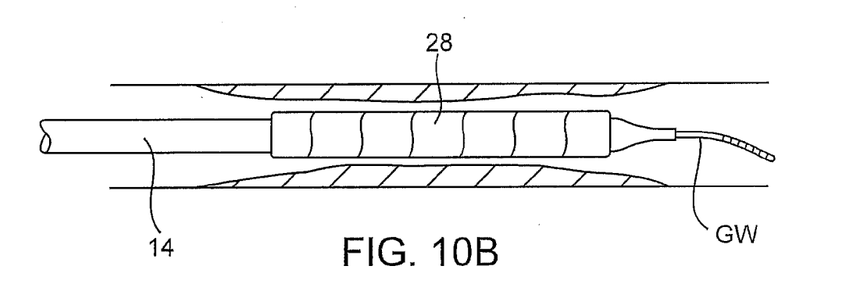
Figure 10C:
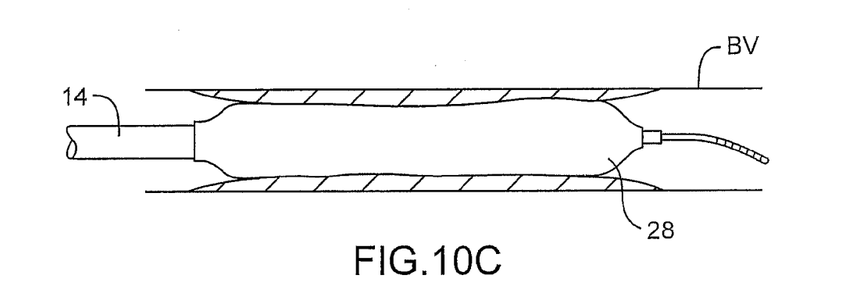

Referring now to FIGS. 10A to 10C, methods for treating a target portion TP of a blood vessel BV can be understood. Catheter 14 is introduced over a guidewire GW, so that balloon 28 is positioned within the blood vessel BV adjacent the target portion TP.

The use of cooling before and/or during dilation of a lesion may allow the use of dilation balloon inflation pressures which are lower than those typically applied for uncooled balloon angioplasty. In some embodiments, inflating balloon 28 at a pressure of about 8 atm and cooling the engaged vessel wall tissues to a temperature between about −2° C. and −12° C., ideally to −10° C., can open a stenotic lesion while inhibiting recoil and/or restenosis. Some lesions, particularly heavily calcified or fibrotic lesions, benefit from higher pressures. It may be advantageous to first dilate the lesion at a slow inflation rate so as to limit any damage to the vessel wall. If dilation of the vessel is not successfully at an initial lower pressure, a second higher pressure (optionally followed by a third even higher pressure) dilation may be desirable. Inflation rates may be controlled between two or more dilation pressures.

While use of multiple pulses of a minimum delivery pulse width to deliver cryogenic cooling fluids such as nitrous oxide are described above, alternative embodiments may also be implemented. For example, the amount of gas delivered using a minimum delivery pulse may be characterized, and larger pulses may be derived from the minimum delivery pulse to selectively and controllably deliver a larger desired amount of cooling fluid during at least a portion of the inflation cycle.

In probe system 10 described above, the cooling fluid supply has a limited quantity. While a vent valve 72 (see FIG. 4) can vent cooling fluid prior to the cooling fluid entering the tissue treatment balloon (or other vaporization chamber) so as to control pressure and/or temperature, this releases the cooling fluid to the atmosphere and limits the treatments that can be provided from the fixed container size. By instead making use of the individual valve performance capabilities in system 10, less gas may be vented so that more gas passes through the cooling balloon and is actually used for treating the tissue. In many embodiments, despite providing a smooth and gradual balloon inflation rate of less than 5 psi/sec., a majority of cooling fluid passes through the balloon, optionally being over 75% of the cooling fluid, and in some embodiments, more than 90% of the cooling fluid passes through the balloon. Hence, it will be possible to run balloons having larger volumes, longer treatment cycles, more discrete treatments, or the like from the same limited cooling fluid supply.

While the exemplary embodiments have been described in some detail, by way of example and for clarity of understanding, those of skill in the art will recognize that a variety of modification, adaptations, and changes may be employed Hence, the scope of the present invention should be limited solely by the appending claims.

What is claimed is:

1. A system for cryogenic treatment of tissue, the system comprising:
   a controller, the controller comprising:
      a pulse width scan module, the pulse width scan module configured to implement a pulse width scan, the pulse width scan determining a command pulse width;
      a treatment protocol module, the treatment protocol module configured to establish a treatment protocol based on the command pulse width received from the pulse width scan module;
      a treatment implementation module, the treatment implementation module configured to effect a desired cryogenic tissue treatment, the treatment implementation module in communication with the treatment protocol module;
   a fluid path, the fluid path extending from a reservoir of fluid to a balloon of a balloon catheter and then to an exhaust lumen;
   a solenoid, the solenoid controlling flow of fluid along the fluid path from the reservoir of fluid to the balloon, the solenoid in communication with the controller; wherein the command pulse width comprises a minimum measured pulse width of the solenoid and
   a pressure sensor, the pressure sensor monitoring pressure of the fluid in the exhaust lumen, the pressure sensor in communication with the controller.

2. The system of claim 1, the controller further comprising a clock, the clock in communication with the treatment implementation module.

3. The system of claim 1, the solenoid being in communication with the pulse width scan module of the controller and with the treatment protocol module of the controller.

4. The system of claim 1, the pressure sensor being in communication with the pulse width scan module of the controller and with the treatment protocol module of the controller.

5. The system of claim 1, wherein the controller includes a processor, the processor programmed with a set of instructions for the pulse width scan module, the set of instructions for the pulse width scan module comprising:
   setting a first pulse width having an initial value;
   measuring a starting pressure in the exhaust lumen with the pressure sensor;
   delivering the first pulse width to the solenoid;
   measuring an end exhaust pressure in the exhaust lumen resulting from the first pulse width with the pressure sensor;
   comparing the end exhaust pressure to the starting exhaust pressure to determine if a threshold change in pressure has been produced.

6. The system of claim 5, wherein the set of instructions for the pulse width scan module further comprises:
   setting a second pulse width which is greater than the first pulse width if the threshold change was not produced;
   measuring an exhaust pressure in the exhaust lumen with the pressure sensor;
   delivering the second pulse width to the solenoid;
   measuring an end exhaust pressure resulting from the second pulse width with the pressure sensor; and comparing the end exhaust pressure to the starting exhaust pressure to determine if a threshold change in pressure has been produced.

7. The system of claim 5, wherein the set of instructions for the pulse width scan module further comprises:
transmitting a command pulse width to the treatment protocol module if the threshold change was produced, the command pulse width being the first pulse width.

8. The system of claim 1, the processor further programmed with a set of instructions for the treatment implementation module, the set of instructions for the treatment implementation module comprising:
transmitting the command pulse width to the solenoid;
measuring an exhaust pressure in the exhaust lumen with the pressure sensor;
comparing the measured exhaust pressure to a target pressure.

9. The system of claim 8, the set of instructions for the treatment implementation module further comprising
transmitting the command pulse width to the solenoid if the target pressure was not reached;
measuring an exhaust pressure in the exhaust lumen with the pressure sensor;
comparing the measured exhaust pressure to the target pressure.

10. The system of claim 1, wherein the treatment protocol module is configured to transmit a plurality of command pulse widths to the solenoid, each command pulse width causing the solenoid to open thereby allowing fluid from the reservoir of fluid to flow along the fluid path to the balloon.

11. The system of claim 1, wherein the reservoir of fluid is maintained at a pressure greater than 650 psi.

12. The system of claim 1, further comprising a housing, the housing comprising the controller, the fluid reservoir, the solenoid, and a portion of the fluid pathway.

13. The system of claim 12, the housing engaged to the balloon catheter.

14. The system of claim 1, the system further comprising a pressure control portion, the pressure control portion comprising the reservoir of fluid, the solenoid, the fluid path, the balloon, the exhaust lumen, a pressure relief valve and a vent valve;
the pressure relief valve configured to control the release of fluid from the exhaust lumen; and
the vent valve configured to limit the flow of fluid to the balloon.

15. The system of claim 1, the system further comprising a fluid shut off portion, the fluid shut off portion comprising the solenoid, a vacuum switch, and a battery;
the vacuum switch being connected to the solenoid by a circuit powered by the battery.

16. The system of claim 1, wherein the command pulse width is a measured characteristic of the solenoid in situ.

17. The system of claim 1, wherein the pulse width scan comprises a plurality of sequential pulse widths beginning with an initial short pulse width and increasing by a step size.

18. The system of claim 1, wherein the plurality of pulse widths successively increases from an initial short pulse width.

19. The system of claim 1, wherein the command pulse width further comprises a small safety factor.

20. A system for cryogenic treatment of tissue, the system comprising:
a fluid path, the fluid path extending from a reservoir of fluid to a balloon of a balloon catheter and then to an exhaust lumen;
a solenoid, the solenoid controlling flow of fluid along the fluid path from the reservoir of fluid to the balloon;
a pressure sensor, the pressure sensor monitoring pressure of the fluid in the exhaust lumen;
a controller in communication with the solenoid and the pressure sensor, the controller comprising:
a pulse width scan module configured to determine a minimum electrical pulse for the solenoid in situ;
a treatment protocol module configured to establish a treatment protocol based on the minimum electrical pulse determined by the pulse width scan module;
a treatment implementation module to implement the treatment protocol, the treatment implementation module in communication with the treatment protocol module.

* * * * *